United States Patent
Santori et al.

[11] Patent Number: 5,971,986
[45] Date of Patent: Oct. 26, 1999

[54] INTRAMEDULLARY DEVICE FOR PINNING BONES

[76] Inventors: Francesco Saverio Santori, Via Ronciglione, 9, 00191 Roma; Marco Tonci Ottieri, Via E. Manfredi, 9, 00197 Roma, both of Italy

[21] Appl. No.: 09/029,234
[22] PCT Filed: Jul. 23, 1997
[86] PCT No.: PCT/IT97/00183
§ 371 Date: Mar. 28, 1998
§ 102(e) Date: Mar. 28, 1998
[87] PCT Pub. No.: WO98/03124
PCT Pub. Date: Jan. 29, 1998

[30] Foreign Application Priority Data

Jul. 23, 1996 [IT] Italy .................................. TO96A0638

[51] Int. Cl.⁶ .................................................... A16B 17/00
[52] U.S. Cl. ................................ 606/62; 606/72; 606/63
[58] Field of Search .............................. 606/62, 61, 63, 606/64, 65, 72, 73

[56] References Cited

U.S. PATENT DOCUMENTS 5,702,397  12/1997  Goble et al. ............................. 606/72
5,814,047  9/1998  Emilio et al. ............................ 606/62

FOREIGN PATENT DOCUMENTS 0561295  9/1993  European Pat. Off. .
95/31942  11/1995  WIPO .

*Primary Examiner*—Michael Buiz
*Assistant Examiner*—(Jackie) Tan-Uyen T. Ho
*Attorney, Agent, or Firm*—Venable; George H. Spencer

[57] ABSTRACT

An intramedullary device (1) for pinning bones, wherein an elongated body (6), insertable inside the medullary canal of the bone (2), is connected to the bone (2) by a connecting device (14) having at least one deformable metal pin (15), and an assembly (16) for deforming and guiding the pin (15) along a respective given path (19); the guide assembly (16) having at least one guide surface (23) extending at least along a portion of the path (19), and a radial constraint element (28) distinct from the elongated body (6) and connected to the elongated body (6) in a position facing an intermediate portion of the guide surface (23) to define, in use, a radial constraint for the pin (15).

18 Claims, 4 Drawing Sheets

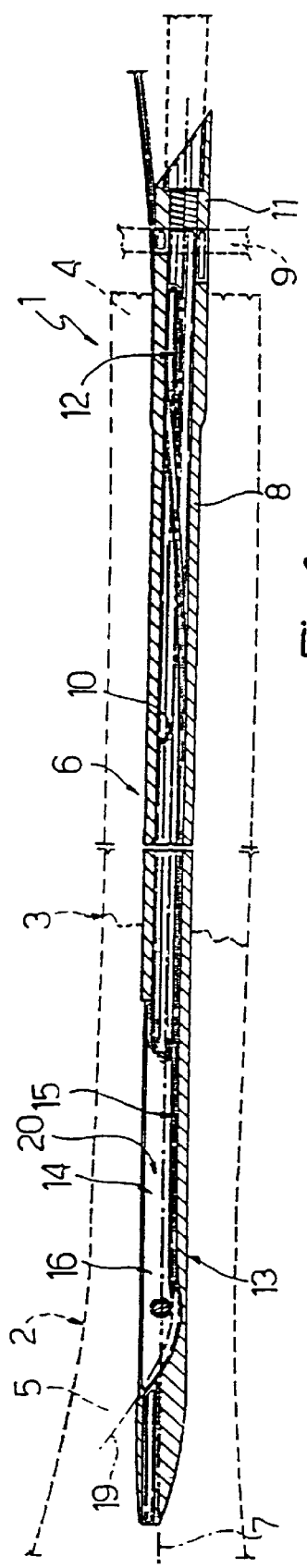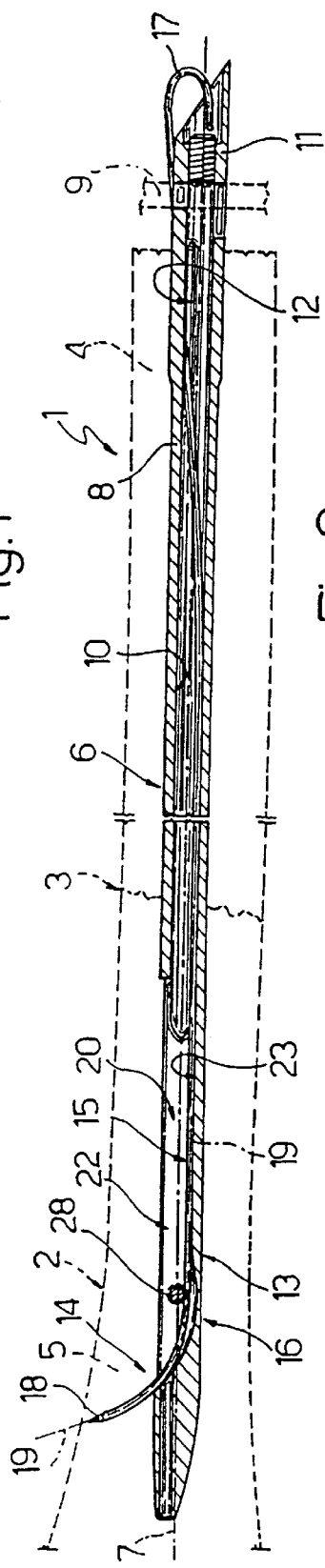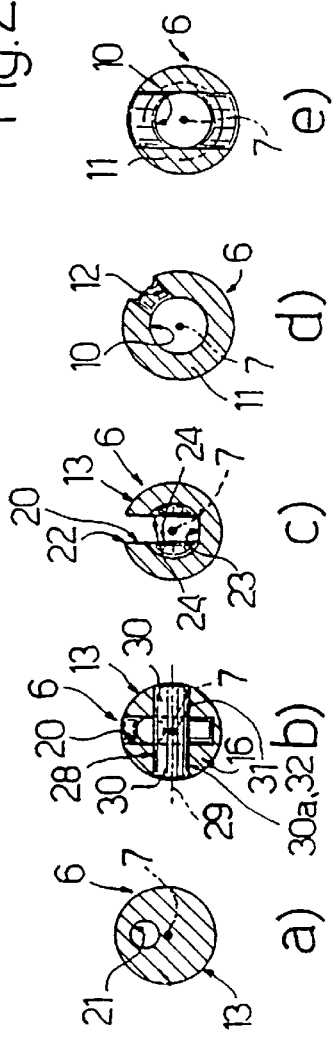

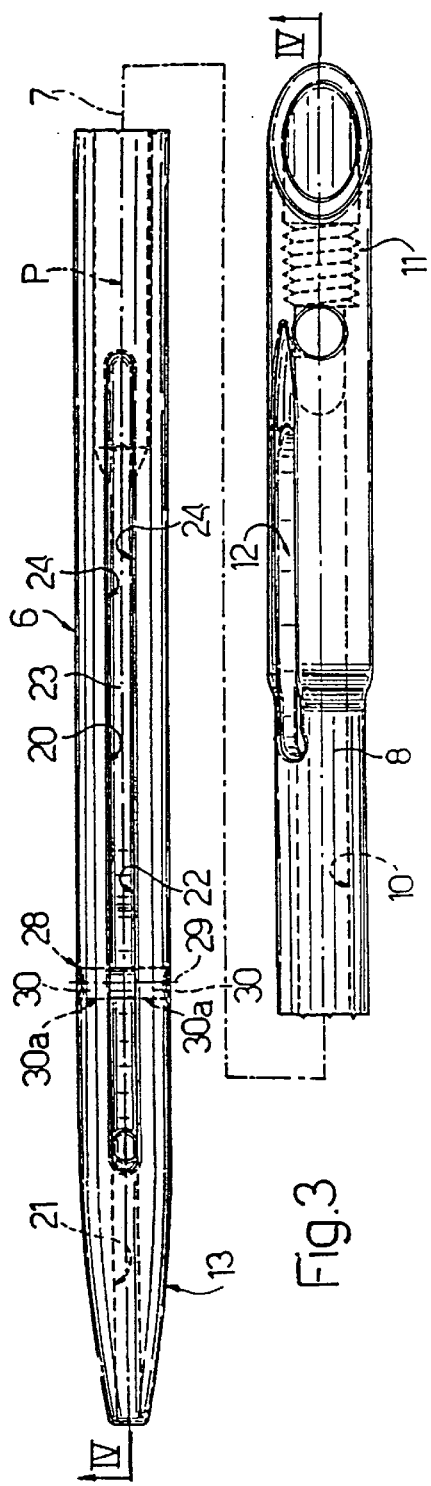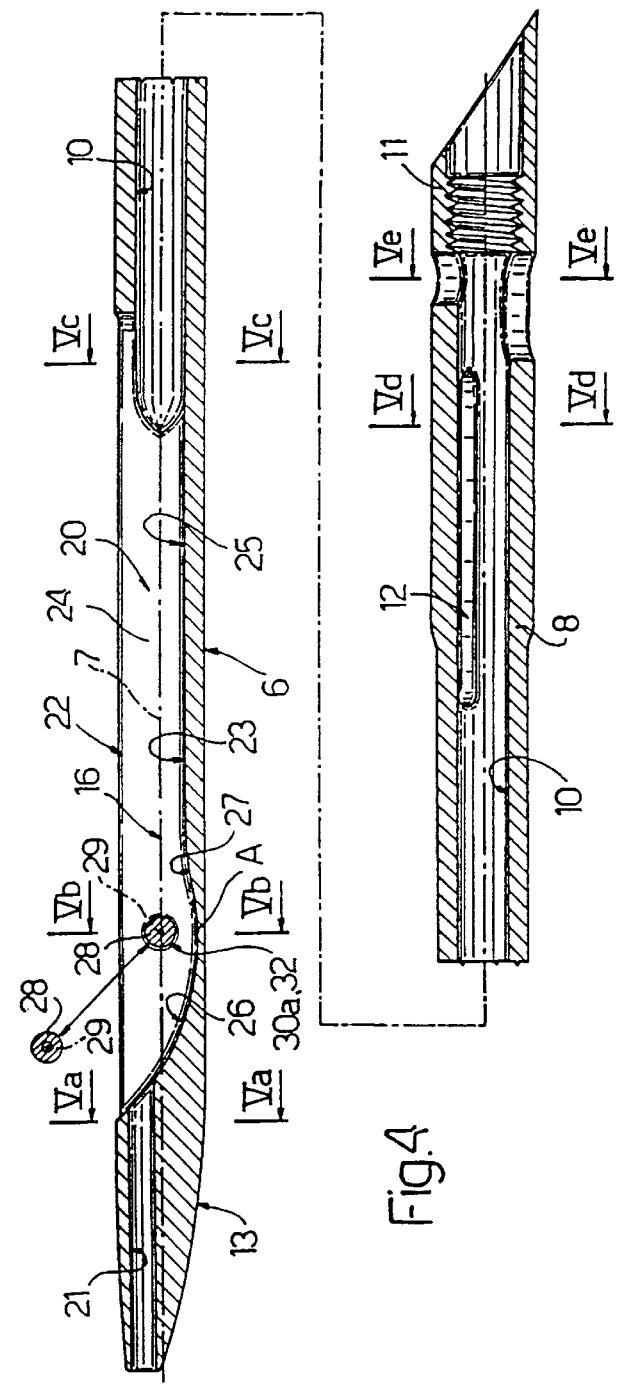
Fig.3
Fig.4

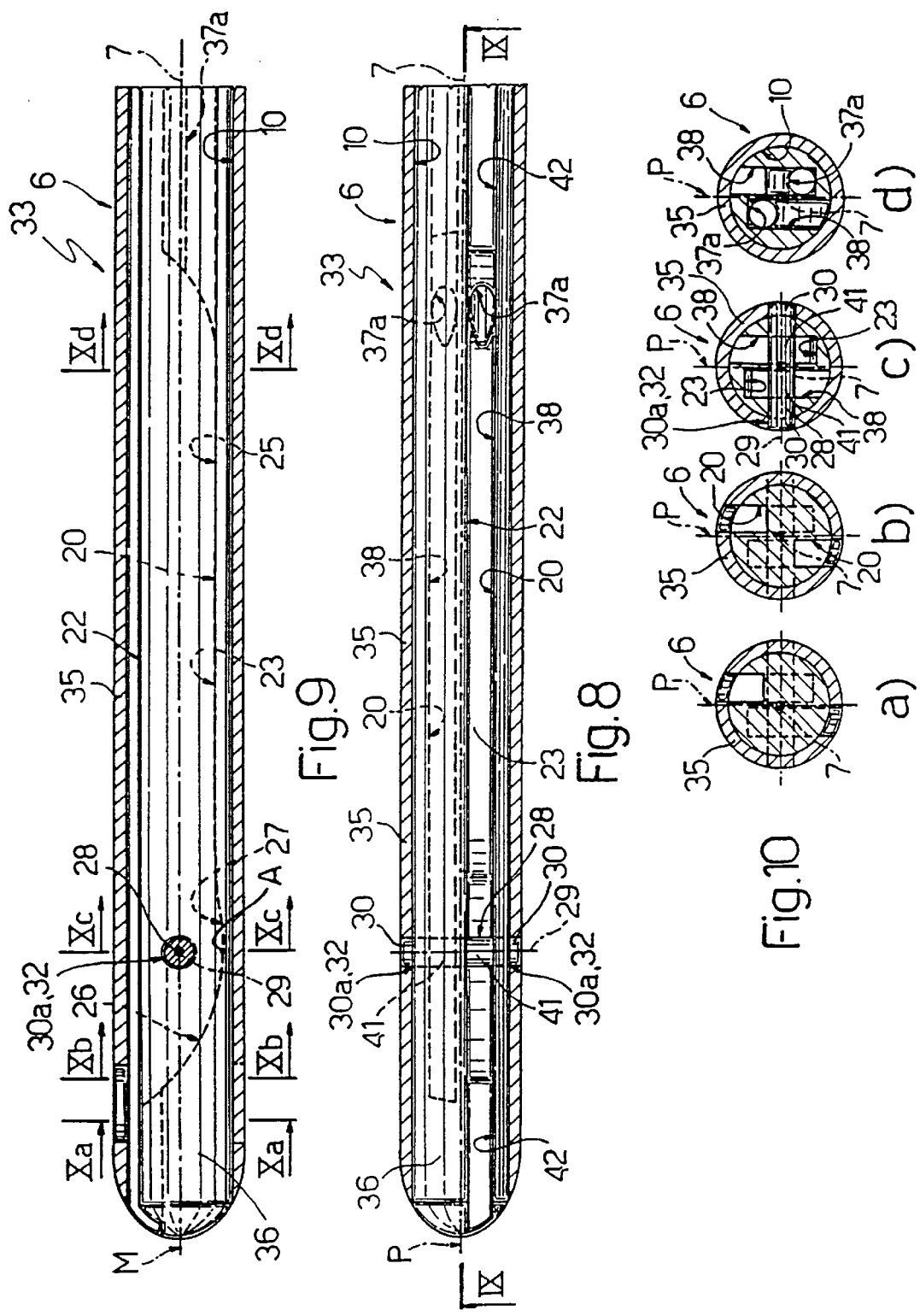

INTRAMEDULLARY DEVICE FOR PINNING BONES

TECHNICAL FIELD

The present invention relates to an intramedullary device for pinning bones.

In particular, the present invention may be used to advantage, though not exclusively, in the treatment of long bones, such as the femur and/or humerus, to which the following description refers purely by way of example.

BACKGROUND ART

For bone treatment in general, a pinning device, as described in Patent Application n. TO94A000407 filed on May 20, 1994 by the present Applicant, is used comprising a cannulate metal rod, which is inserted inside the medullary canal of the bone; and an anchoring or pinning assembly for releasably connecting one or both end portions of the cannulate rod to respective portions of the bone.

The anchoring assembly comprises two or more deformable metal pins and, for each pin, a respective guide conduit formed inside the cannulate rod. Each conduit has an inside diameter approximately equal to but no smaller than the outside diameter of the respective pin, so as to guide the pin along a given path, and the pins are connected positively to a common slide, which is movable from the outside by means of a mechanical device for moving the pins simultaneously to and from a forward pinning position, in which respective deformed end portions of the pins project outwards from the rod and are inserted in use, inside the respective bone portion.

Though widely used, by permitting withdrawal of the pins from the bone when the fracture heals, known devices of the above type are not altogether satisfactory, mainly on account of the considerable force normally required to remove the pins.

This is substantially due to the inside diameter of each guide conduit being comparable with the outside diameter of the respective pin, so that, when withdrawing the pin, fairly severe friction components opposing withdrawal are generated between the pin and the conduit. For this reason, the pins are connected to said mechanical device, which not only increases the cost of producing the device, but, by comprising a single slide common to all the pins, also creates problems when, for various reasons, the pins must be withdrawn separately.

Moreover, the conduits of known devices of the above type are at times fairly difficult to form, due to their normally being formed by drilling and subsequently milling a solid portion of the rod.

DISCLOSURE OF INVENTION

It is an object of the present invention to provide a straightforward, low-cost intramedullary device, designed to overcome the aforementioned drawbacks.

According to the present invention, there is provided an intramedullary device for pinning bones, the device comprising an elongated body insertable inside a bone and having a respective axis; and connecting means for connecting said elongated body to the bone; said connecting means comprising at least one deformable pin, and guide means for guiding said pin along a respective given path into an extracted operating position wherein the pin projects outwards of said elongated body; and said guide means comprising a guide surface extending along at least a portion of said path; characterized in that said guide means also comprise radial constraint means distinct from said elongated body, located facing and at a distance from said guide surface, and having a supporting portion for supporting said pin and which is smaller than said guide surface; fastening means being provided for connecting said constraint means to said elongated body.

BRIEF DESCRIPTION OF DRAWINGS

A number of non-limiting embodiments of the present invention will be described by way of example with reference to the accompanying drawings, in which:

FIGS. 1 and 2 show longitudinal sections of a first preferred embodiment of the intramedullary device according to the present invention, as applied to a humerus and in two different operating positions;

FIG. 3 shows a larger-scale side view of a detail in FIGS. 1 and 2;

FIG. 4 shows a section along line IV—IV in FIG. 3;

FIGS. 5a to 5e show sections along respective lines a—a, b—b, c—c, d—d, e—e in FIG. 4;

FIG. 8 shows a section of a detail in FIGS. 6 and 7;

FIG. 9 shows a section along line IX—IX in FIG. 8;

FIGS. 10a to 10d show sections along respective lines a—a, b—b, c—c, d—d in FIG. 9.

BEST MODE FOR CARRYING OUT THE INVENTION

Figure 6:
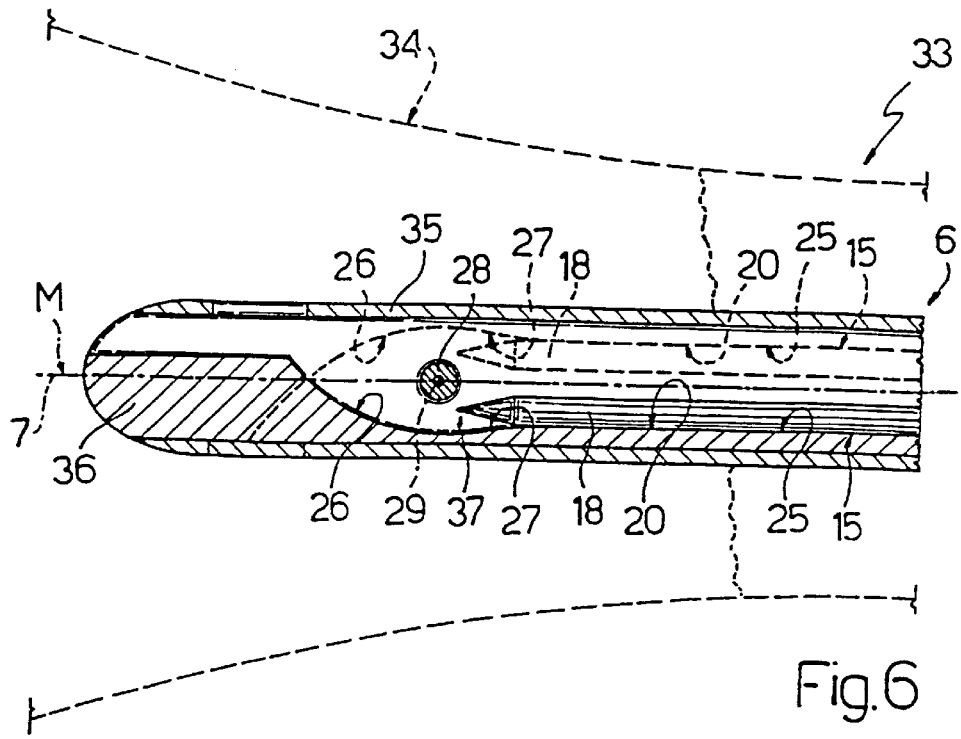
FIGS. 6 and 7 show partial longitudinal sections of a second preferred embodiment of the intramedullary device according to the present invention, as applied to a femur and in two different operating positions.

Number 1 in FIGS. 1 and 2 indicates an intramedullary device for the treatment of a fractured or fracture-threatened bone.

In the example shown, device 1 is used to treat a humerus 2 having a break focus 3 between a proximal portion 4 and distal portion 5 of humerus 2.

As shown in FIGS. 1 and 2 and particularly in FIGS. 3 and 4, device 1 comprises a preferably metal rod 6 having a respective axis 7, and which is inserted inside the medullary canal of humerus 2. Rod 6 comprises a tubular, substantially cylindrical first portion 8, which, in the example shown, extends partially inside proximal portion 4 of humerus 2, is connected integrally to proximal portion 4 in known manner, normally by means of a through screw 9, and defines a conduit 10 coaxial with axis 7. Again with reference to FIGS. 3 and 4, portion 8 comprises a fully threaded end portion 11, which is connected to a known device (not shown) for inserting/withdrawing rod 6 into/from the medullary canal; and an elongated longitudinal lateral opening 12 by which conduit 10 communicates externally Rod 6 also comprises an elongated second portion 13, which, in use, extends partially inside distal portion 5 of humerus 2, and is connected releasably to distal portion 5 by an anchoring device 14 (FIGS. 1 and 2).

Device 14 comprises a metal, preferably circular-section pin 15; and a deforming and guide assembly 16 for guiding pin 15 between a withdrawn idle position (FIG. 1), wherein pin 15 extends at least partially inside conduit 10 and projects outwards of conduit 10 through opening 12, and an extracted or advanced position (FIG. 2), wherein pin 15 still engages opening 12 and has an end portion 17 turned inside tubular portion 8, and an opposite end portion 18 extending outwards of rod 6 and inserted, in use, inside distal portion 5 of humerus 2.

More specifically, guide assembly 16 guides pin 15 between said withdrawn and extracted positions along the same given path 19 (FIGS. 1 and 2), or guides pin 15 into the extracted position along given path 19, and into the withdrawn position along a number of alternative paths other than path 19.

Again with reference to FIGS. 1 to 4 and FIGS. 5b and 5c, assembly 16 comprises a longitudinal channel 20 extending along an intermediate portion of portion 13 along path 19, and which communicates axially with an outlet of conduit 10, communicates axially with a through hole 21 parallel to axis 7 for the passage of a known guide wire (not shown), and communicates laterally with the outside through an elongated longitudinal opening 22 (FIGS. 4 and 5c).

Channel 20 is defined by a bottom surface 23, and by two flat lateral surfaces 24 (FIGS. 3 and 4) parallel to each other and to axis 7 and separated by a distance approximately equal to but no smaller than the outside diameter of pin 15, and has a U-shaped cross section (FIG. 5c) elongated in a direction parallel to surfaces 24 and perpendicular to axis 7.

As shown, particularly in FIGS. 4, 5b and 5c, bottom surface 23 comprises, in cross section perpendicular to axis 7, a substantially straight first profile perpendicular to lateral surfaces 24. Alternatively, according to a variation not shown, said bottom profile is C-shaped with its concavity facing longitudinal opening 22 of channel 20, and with a radius of curvature approximately equal to but no smaller than the outside radius of pin 15. Surface 23 also comprises a second profile obtained by intersecting surface 23 with a plane P through axis 7 and parallel to surfaces 24 (FIG. 3), and having a substantially straight first end portion 25 extending from the outlet of conduit 10. The second profile also comprises a second curved ramp end portion 26 with its concavity facing opening 22 of channel 20; and a curved intermediate third portion 27 so shaped that the distance between the starting point A of ramp portion 26 and opening 22 is greater than that between straight portion 25 and opening 22. As such, the depth of channel 20 is substantially constant along the whole of portion 25, increases at portion 27 up to a maximum at point A, and then decreases gradually to zero along portion 26.

With reference to FIGS. 4 and 5b, assembly 16 also comprises a solid or tubular pin 28 (FIG. 4), which has an axis 29 intersecting axis 7 and perpendicular to plane P and path 19, and extends, at a distance from surface 23, substantially at point A, i.e. at the deepest point of channel 20 (FIG. 4).

Pin 28 comprises two lateral portions 30, which engage respective holes formed in portion 13, and are connected to the holes by a frictional push connection 30a, or in rotary manner so as to define a hinge 32 permitting pin 28 to rotate, in use, about axis 29 with respect to rod 6. Pin 28 also comprises an intermediate portion 31 extending between surfaces 24, and which defines part of path 19 and a radial constraint against which pin 15 cooperates at a single point of contact. In other words, intermediate portion 31 defines, with a facing portion of surface 23, a window of a transverse size approximately equal to but no smaller than the outside diameter of pin 15, and through which pin 15 slides.

Operation of device 1 will now be described as of the FIG. 1 condition, wherein rod 6 is inserted inside the medullary canal of humerus 2, end portion 18 of pin 15 is positioned contacting portion 25, and the rest of pin 15 extends inside conduit 10 and projects outwards of conduit 10 through opening 12.

As of the above condition, using portion 17 of pin 15 projecting outwards of rod 6, pin 15 is fed in known manner along path 19 into the extracted position. As it is fed forward, pin 15 first travels along surface 23, and is then inserted spontaneously between surface 23 and pin 28, which defines a radial constraint by which pin 15 is fed forward in contact with both surface 23 and pin 28, if pin 28 is locked with respect to rod 6. Conversely, if pin 28 is fitted to rotate about axis 29, the friction between pin 28 and pin 15 is converted from sliding to rolling friction, thus greatly reducing the effort required to push pin 15 along path 19. Once the extracted position is reached, portion 17 of pin 15 still projecting outwards of rod 6 is bent into a loop and inserted inside portion 11 as shown in FIG. 20.

Once humerus 2 is healed, the bent end portion 17 of pin 15 is engaged in known manner and pin 15 withdrawn through opening 12.

If, for any reason, withdrawal of pin 15 proves difficult, and in particular requires considerable force despite the rotation of pin 28, pin 28 may be located, e.g. by x-ray, and, being connected to rod 6 by a frictional push connection, may be removed axially from rod 6 by means of a straightforward punch.

On disengaging channel 20, pin 28 frees pin 15 radially, so that pin 15 moves crosswise to path 19 inside channel 20 and towards longitudinal opening 22 into a new configuration of minimum resistance to withdrawal.

The embodiment shown in FIGS. 6 to 10 relates to an intramedullary device 33 similar to device 1, and the component parts of which are indicated wherever possible using the same numbering system as for the corresponding parts of device 1.

Device 33 may be used to advantage for pinning a femur 34 (FIGS. 6 and 7), and differs from device 1 by rod 6 comprising a tubular portion 35 as opposed to portion 13, and by comprising a body or insert 36 housed inside tubular portion 35 and connected integrally to portion 35 by means of pin 28.

In the example shown, insert 36 forms part of a crosspinning anchoring device 37, which differs from device 14 by comprising two pins 15, and two identical longitudinal guide channels 20, which, as shown clearly in FIGS. 8 and 10, are formed inside insert 36, opposite each other and on opposite sides of said plane P perpendicular to axis 29 of pin 28. Channels 20 comprise respective axial inlets, which communicate with conduit 10 through respective axial holes 37a (FIGS. 8 and 9) formed in insert 36 and each substantially tangent to bottom surface 23 of respective channel 20. Longitudinal openings 22 of channels 20 are partially closed by tubular portion 35 to define respective guide conduits 38 (FIGS. 10c and 10d), which, as shown in FIGS. 6 and 7, comprise respective straight portions 39 on opposite sides of a plane M containing axes 7 and 29, and communicate externally through respective openings 40, each formed in portion 35 on the opposite side of plane M to the respective straight portion 39.

Figure 7:
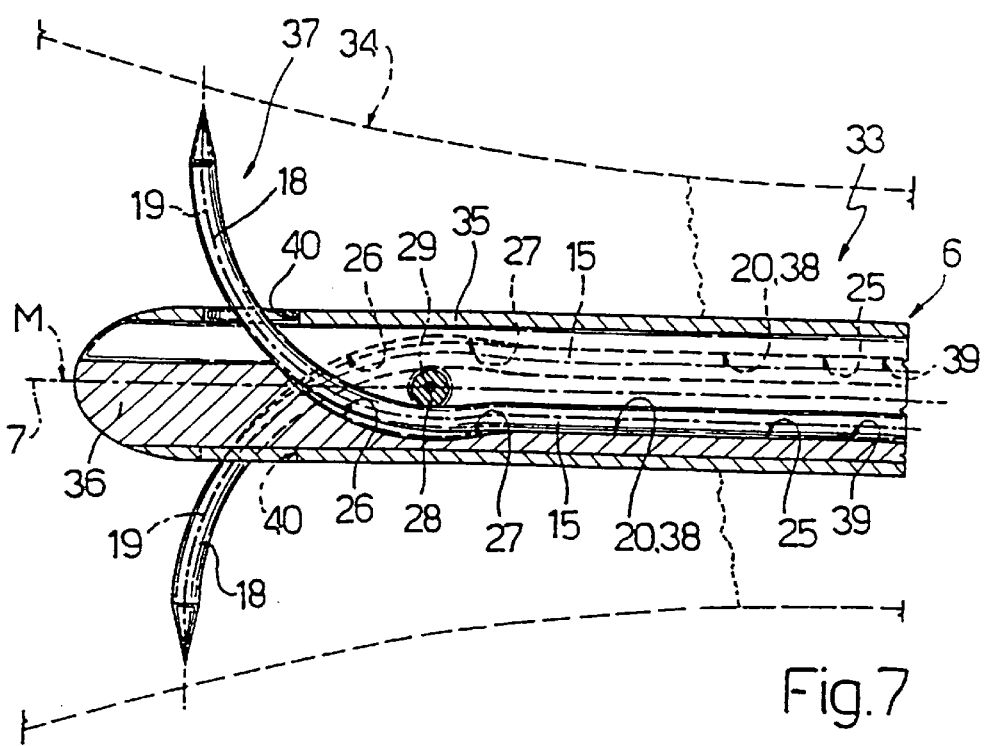

As shown, particularly in FIG. 7, pin 28 extends between pins 15, when pins 15 are in the extracted position, and comprises intermediate portions 41 (FIG. 10c) facing and separated by a distance from respective bottom surfaces 23, and located in substantially the same position as intermediate portion 31 of pin 28 of device 1 to define respective radial constraints for respective pins 15.

With reference to FIGS. 6 to 9, insert 36 also comprises two grooves 42 (FIG. 8), which constitute axial extensions in opposite directions of one of channels 20, and are closed by portion 35 to define respective coaxial conduits eccentric with respect to axis 7 and for enabling external communication of the relative guide conduit 38, and defining, with conduit 38, a passage for a known guide wire (not shown).

As compared with known devices, devices 1 and 33 therefore clearly provide for both pushing pins 15 with relatively little effort along respective given paths 19 into the extracted positions, and for equally easily removing pins 15 from the bone when the fracture heals.

In fact, using a single cylindrical pin 28 as a radial constraint or means of guiding pins 15 provides, above all, for greatly reducing the contact and sliding surface between pins 15 and the guide assembly—pins 15 and pin 28 in fact cooperate at a very small, even punctiform, contact region—thus greatly reducing the friction components opposing the travel of pins 15.

Moreover, when a single pin 15 is provided, and pin 28 is connected to rod 6 so as to rotate about axis 29, said friction components are further reduced by being converted from sliding to rolling friction.

Finally, by providing a pin 28 connected releasably to rod 6, i.e. which may simply be withdrawn axially from the rod, and a guide channel 20 elongated in a direction perpendicular to axis 7 of rod 6 and to axis 29 of pin 28, the path of each pin 15 may conveniently be varied during withdrawal That is, in the absence of pin 28, each pin 15 is free to move crosswise to and away from bottom surface 23 of channel 20, thus greatly reducing the contact surface, and hence friction, between pin 15 and the guide surface.

As compared with known solutions, the marked reduction in friction, and hence in the force applied externally to move pins 15 with respect to rod 6, provides for eliminating the mechanical devices associated with rod 6, and, in the case of a number of pins 15, for withdrawing pins 15 separately one after the other and along different paths.

Devices 1 and 33 therefore clearly provide for feeding each pin 15 into the extracted position along any given or desired path. The course of paths 19, in fact, depends on the geometry of bottom surface 23 of respective channel 20, so that, since surface 23 is formed by simply externally milling a portion of rod 6 or insert 36, the geometry of surface 23 may be varied by simply controlling the position of the milling cutter accordingly. The course of paths 19 also depends on the position of pin 28 with respect to bottom surface 23 of respective channel 20, which position may be selected as required, according to the path along which end portions 18 of pins 15 are to be fed inside bone 2, 34.

Clearly, changes may be made to devices 1, 33 as described and illustrated herein without, however, departing from the scope of the present invention. In particular, bottom surfaces 23 of channels 20 may be shaped differently from that described herein by way of example; the location of pin 28 with respect to surface 23 may differ from that described; provision may be made for a number of pins 28, e.g. adjacent to one another; or pin 28 may be replaced with other movable and/or releasable radial constraint elements capable of varying a predetermined path.

Finally, device 1 may comprise more than one pin 15, e.g. two, just as device 33 may comprise a single pin 15.

We claim:

1. An intramedullary device (1; 33) for pinning bones, the device comprising an elongated body (6) insertable inside a bone (2; 34) and having a respective axis (7); and connecting means (14; 37) for connecting said elongated body (6) to the bone (2; 34); said connecting means (14; 37) comprising at least one deformable pin (15), and guide means (16) for guiding said pin (15) along a respective given path (19) into an extracted operating position wherein the pin (15) projects outwards of said elongated body (6); and said guide means (16) comprising a guide surface (23) extending along at least a portion of said path (19); wherein in that said guide means (16) also comprise radial constraint means (31; 41) distinct from said elongated body (6), located facing and at a distance from said guide surface (23), and having a supporting portion for supporting said pin (15) and which is smaller than said guide surface (23); fastening means (30a, 32) being provided for connecting said constraint means (31; 41) to said elongated body (6).

2. A device as claimed in claim 1, wherein in that said fastening means (30a, 32) are releasable fastening means (30a) permitting displacement of said constraint means (31; 41) with respect to said guide surface (23) and a variation of said given path (19).

3. A device as claimed in claim 2, wherein in that said releasable fastening means comprise a friction connection (30a).

4. A device as claimed in claim 3, wherein in that said friction connection (30a) is a sliding push connection.

5. A device as claimed in claim 1, wherein in that said fastening means (30a, 32) comprise hinge means (32) having a hinge axis (29) crosswise to said given path (19).

6. A device as claimed in claim 1, wherein in that said constraint means (31; 41) are located facing an intermediate portion of said guide surface (23) to define, with said intermediate portion, a window through which said pin (15) travels in use.

7. A device as claimed in claim 6, wherein in that said pin (15) and said constraint means (31; 41) cooperate with each other in contacting manner substantially at a single point of contact.

8. A device as claimed in claim 1, wherein in that said constraint means (31; 41) comprise at least one cylindrical pin (28) located at least partially facing said guide surface (23), and having a respective axis (29) extending crosswise to said given path (19).

9. A device as claimed in claim 8, wherein in that the axis (29) of said cylindrical pin (28) extends perpendicularly to said given path (19).

10. A device as claimed in claim 8, wherein in that the axis (29) of said cylindrical pin (28) intersects the axis (7) of said elongated body (6).

11. A device as claimed in claim 1, wherein in that said cylindrical pin (28) is a tubular pin.

12. A device as claimed in claim 1, wherein in that said guide means (16) comprise a channel (20) extending along at least part of said path (19), and said guide surface (23) defines the bottom surface of said channel (20); the channel (20), in cross section, being elongated in a direction crosswise to the axis (29) of said cylindrical pin (28) and substantially perpendicular to the axis (7) of said elongated body (6).

13. A device as claimed in claim 1, wherein in that said elongated body (6) comprises a first tubular portion (8) having a lateral opening (12) for insertion of said pin (15).

14. A device as claimed in claim 13, wherein in that said pin (15), when in said extracted operating position, has an end portion (17) projecting outwards of said first tubular portion (8) through said lateral opening (12).

15. A device as claimed in claim 14, wherein in that said end portion (17) projecting through said lateral opening (12) is bent partially and inserted inside said first tubular portion (8) at least when said pin (15) is in the extracted operating position.

16. A device as claimed in claim 1, wherein in that said connecting means (37) comprise two said pins (15) and, for each of said pins (15), a respective guide surface (23); said radial constraint means comprising a single cylindrical pin (28) extending crosswise to said relative path (19) and between said pins (15), at least when said pins (15) are in the extracted operating position.

17. A device as claimed in claim 16, wherein in that said guide surfaces (23) define the bottom surfaces of respective guide channels (20) comprising respective first portions (39) located on opposite sides of a plane (M) containing the axis (7) of said elongated body (6) and the axis (29) of said cylindrical pin (28).

18. A device as claimed in claim 17, wherein in that said elongated body (6) comprises a second tubular portion (35); and in that said connecting means (37) also comprise an insert (36) distinct from said elongated body (6) and inserted at least partially inside said second tubular portion (35); said channels (20) being formed in said insert (36), and being closed by said second tubular portion (35) to define respective guide conduits (38) communicating externally through respective openings (40) formed in said second tubular portion (35); said cylindrical pin (28) being withdrawable from the outside even when the elongated body (6) is inserted inside the medullary canal of the respective bone (2; 34).

\* \* \* \* \*